(12) United States Patent
Shroff et al.

(10) Patent No.: US 8,309,765 B2
(45) Date of Patent: Nov. 13, 2012

(54) PROCESS FOR MANUFACTURE OF HIGH PURITY D-(−)-N,N-DIETHYL-2-(α-NAPHTHOXY) PROPIONAMIDE

(75) Inventors: Jaidev Rajnikant Shroff, Maharashtra (IN); Vikram Rajnikant Shroff, Maharashtra (IN); Narendra Purushottam Karambelkar, Maharashtra (IN)

(73) Assignee: United Phosphorus Limited, Gujarat (IN)

( * ) Notice: Subject to any disclaimer, the term of this patent is extended or adjusted under 35 U.S.C. 154(b) by 449 days.

(21) Appl. No.: 12/598,752

(22) PCT Filed: May 5, 2008

(86) PCT No.: PCT/IN2008/000284
§ 371 (c)(1),
(2), (4) Date: Nov. 3, 2009

(87) PCT Pub. No.: WO2009/004642
PCT Pub. Date: Jan. 8, 2009

(65) Prior Publication Data
US 2010/0144532 A1 Jun. 10, 2010

(30) Foreign Application Priority Data
May 4, 2007 (IN) .......................... 858/MUM/2007

(51) Int. Cl.
*C07C 231/02* (2006.01)
*C07C 231/12* (2006.01)

(52) U.S. Cl. .......... 564/140; 564/138; 504/338
(58) Field of Classification Search ............ 564/138, 564/140; 504/338
See application file for complete search history.

(56) References Cited

U.S. PATENT DOCUMENTS

| | | |
|---|---|---|
| 3,480,671 A | 11/1969 | Tilles et al. |
| 3,718,455 A | 2/1973 | Baker et al. |
| 3,998,880 A | 12/1976 | Mihailovski et al. |
| 4,548,641 A | 10/1985 | Walker et al. |
| 4,668,628 A | 5/1987 | Dahod et al. |
| 4,766,220 A | 8/1988 | Gras |
| 4,775,753 A * | 10/1988 | Barriere et al. ............ 540/456 |

FOREIGN PATENT DOCUMENTS
CN   1786019   *   6/2006

OTHER PUBLICATIONS

Nielsen et al, J. Med. Chem., 1989, 32(3), 727-734.*
Chan, et al, J. Agric. Food Chem, 23(5), 1008-1010 (1975).
Sugai, T. and Mori, K, Agric. Bio. Chem., 48, 2501 (1984).
Li Jin, et al., Pesticides, 39, 18-20, 2000.

* cited by examiner

*Primary Examiner* — Shailendra Kumar
(74) *Attorney, Agent, or Firm* — Yancy IP Law, PLLC

(57) ABSTRACT

According to one aspect of the present invention there is provided a substantially high purity D-(−)-N,N-diethyl-2-(α-naphthoxy)propionamide and a process for the manufacture of substantially higher purity D-(−)-N,N-diethyl-2-(α-naphthoxy)propionamide having chemical purity near about or above 95%, and chiral purity near about or more than 97%. According to another aspect of the invention is to provide an agrochemical compositions containing highly pure optically active D-(−)-N,N-diethyl-2-(α-naphthoxy)propionamide.

41 Claims, No Drawings

PROCESS FOR MANUFACTURE OF HIGH PURITY D-(−)-N,N-DIETHYL-2-(α-NAPHTHOXY) PROPIONAMIDE

TECHNICAL FIELD

This invention relates to a process for manufacture of high purity D-(−)-N,N-diethyl-2-(α-naphthoxy)propionamide (Herbicide), particularly from L-2-Halopropionic Acid or (S)-(−)-2-Halopropionic Acid. The invention further provides agrochemical compositions containing highly pure optically active D-(−)-N,N-diethyl-2-(α-naphthoxy)propionamide.

BACKGROUND AND PRIOR ART

N,N-diethyl-2-(α-naphthoxy)propionamide is known as napropamide, and its racemic mixture is generally marketed under trade name as "Devrinol". It is used for pre-emergence control of annual grasses and broad-leaved weeds in many crops and plantations.

The second carbon atom at the propionamide group in napropamide has a hydrogen atom, a methyl group, a naphthoxy moiety and a carboxamide group thereby forming a chiral center. Hence the molecule [Fig I] can exist in two chiral stereoisomers: D or (R) and L or (S)-isomers.

Various processes reported in the literature for the synthesis of this compound generally result in producing different mixture of these isomers, usually racemic mixtures and they are difficult to separate.

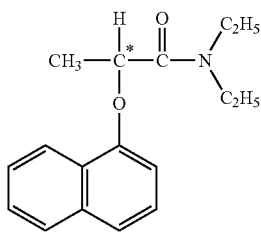

FIG. I

Both D and L isomers and/or their racemic mixtures of the compound N,N-diethyl-2-(α-naphthoxy)propionamide have herbicidal activity. However, Chan et al., J. Agric. Food Chem., 23(5), 1008-1010, (1975), reported that the (D)-isomer of napropamide shows 8 times more activity than the (L)-isomer and 1.7-2 times more than it's racemic mixture, for certain weeds. Thus, effective herbicidal compositions can be made using about half the quantity of the current racemic napropamide.

Various synthetic strategies have been reported for the preparation of optically active 2-arylpropionamide and their different homologues as for e.g., (a) optically active base for resolving recemates. (b) a resolution of diasteromeric derivatives as salts of esters, anhydrides (c) biochemical methods (asymmetric hydrolysis of esters or oxidation of aromatic hydrocarbons (T. Sugai and K. Mori, Agric. Bio. Chem., 48, 2501 (1984)) or (d) stereo-specific reactions where starting material is having chiral center.

Various processes have been reported for the preparation of D-(−)-N,N-diethyl-2-(α-naphthoxy)propionamide. Published literatures relevant to this subject are given below, in chronological order. However, the exact chemical as well as chiral purity of the D-(−) product obtained by some of these processes has not been reported.

U.S. Pat. No. 3,480,671 (1969) (Tilles et al), describes the preparation of racemic N,N-diethyl-2-(α-naphthoxy)propionamide from α-naphthol and N,N-diethyl-bromo propionamide in methanol as solvent and by using sodium methoxide.

U.S. Pat. No. 3,718,455 (1973) (Baker et al) discloses the process for the preparation of the D-isomer of the napropamide. According to this process, the resolution of dl-2-(α-naphthoxy)propionic acid results in d-acid of 90% purity and 1-acid of 85% purity. The process further discloses the conversion of the d-acid into acid chloride in DMF by using phosgene. The acid chloride is then converted into D-isomer of N,N-diethyl-2-(α-naphthoxy)propionamide through the amidation by using diethyl amine and triethyl amine as acid acceptor. The molar yield of D-isomer of N,N-diethyl-2-(α-naphthoxy)propionamide as disclosed in the patent is 61%.

Preparation by this process produced product in overall low yield. The chemical or chiral purity of the product was not addressed by this process. Further, this process involves resolution technique, which is highly expensive and time consuming. Hence, this process is not suitable for commercial manufacture of D-isomer of N,N-diethyl-2-(α-naphthoxy) propionamide.

James H. H Chan et al, J. Agric. Food Chem., 23(5), 1008-1010, (1975), reported the procedure for the D-isomer of the napropamide. The process involves the use of L (+) form of lactic acid as starting material and then conversion into ester and after subsequent reactions into D-isomer of napropamide. This process involves multi steps and overall yield is low. The process is also dependant on the availability of L (+) form of Lactic acid, which is not easily available. Therefore, this process is not suitable for large-scale preparation.

U.S. Pat. No. 3,998,880 (1976) (Simone et al) described the following process of preparing racemic N,N-diethyl-2-(α-naphthoxy)propionamide. The process comprises reacting 2-chloropropionic acid with diethyl amine in the presence of phosphoryl chloride giving an intermediate 2-chloropropionyl diethyl amide, which is then reacted with α-naphthol and sodium hydroxide to give N,N-diethyl-2-(α-naphthoxy)propionamide. However, this process teaches the preparation of racemic N,N-diethyl-2-(α-naphthoxy)propionamide.

U.S. Pat. No. 4,548,641 (1985) (Walker et al) described the two methods for the preparation of optically active isomer of N,N-dialkyl-2-(4-substituted-α-naphthoxy)propionamide. According to the first method, optically active lower alkyl ester of 2-halopropionic acid is reacted with 4-substituted α-naphthol, to produce optically active 4-substituted-α-naphthoxy propionic acid. This acid is then converted into acid chloride by using phosgene and subsequently reacted with dialkyl amine to obtain the desired optically active isomer. This method involving conversion of lower alkyl ester of 2-halopropionic acid to the optically active 4-substituted-α-naphthoxy propionic acid gives low yield and may give some by-product (e.g., furan type ring condensed with a naphthalene ring) which was very difficult to be separated from the desired product.

According to the second method, optically active amide is prepared by reacting an ester with an amine in the presence of a promoter which is halide of a group IIIA metal having molecular weight of 26 or greater, or of a group IVB metal. This dialkylated amide is treated with substituted naphthol to produce a product with desired isomer. The products obtained by this method are not sufficiently rich in optical purity.

Lin Jin et al, Pesticides, 39, 18-20, (2000) reported different resolution process of the preparation of the optically active isomer. These resolution techniques involved very complex, tedious procedures and expensive resolving agents. The resolution techniques also required a large amount of solvent leading to the high cost.

There is therefore a need to make commercially available a highly pure optically active D-(−)-N,N-diethyl-2-(α-naphthoxy)propionamide for better herbicidal activity and a process suitable for making a commercially feasible high purity D-isomer of D-(−)-N,N-diethyl-2-(α-naphthoxy)propionamide.

OBJECTS OF THE INVENTION

It is an object of the present invention to provide the process for the manufacture of D-(−)-N,N-diethyl-2-(α-naphthoxy)propionamide to give a product with high chiral purity and acceptable high yield.

Yet another object of this invention is to provide a process for manufacture of D-(−)-N,N-diethyl-2-(α-naphthoxy)propionamide of further substantially higher chemical purity from the substantially high purity D-(−)-N,N-diethyl-2-(α-naphthoxy)propionamide.

Further object of the invention is to provide a novel process that goes through an intermediate L-(+)-2-halopropionyl chloride.

Yet another object of the invention is to provide a process which is simple and can be used for the large scale production of D-(−)-N,N-diethyl-2-(α-naphthoxy)propionamide.

One more object of the invention is to provide a product D-(−)-N,N-diethyl-2-(α-naphthoxy)propionamide having chemical purity above 90% and chiral purity above 80% may be further raised to higher purity product.

Further object of the invention is to provide an agrochemical composition using higher purity D-(−)-N,N-diethyl-2-(α-naphthoxy)propionamide and the process for preparing the same and for the large scale manufacture with commercial feasibility.

SUMMARY OF THE INVENTION

According to one aspect of the present invention there is provided a substantially high purity D-(−)-N,N-diethyl-2-(α-naphthoxy)propionamide and a process for the manufacture of substantially higher purity D-(−)-N,N-diethyl-2-(α-naphthoxy)propionamide having chemical purity near about or above 95%, and chiral purity near about or more than 97%. According to another aspect of the invention is to provide an agrochemical compositions containing highly pure optically active D-(−)-N,N-diethyl-2-(α-naphthoxy)propionamide.

DESCRIPTION OF INVENTION

The present invention provides substantially highly pure D-(−)-N,N-diethyl-2-(α-naphthoxy)propionamide and a process for the manufacture of substantially highly pure D-(−)-N,N-diethyl-2-(α-naphthoxy)propionamide.

Also, this invention provides agrochemical compositions containing highly pure optically active D-(−)-N,N-diethyl-2-(α-naphthoxy)propionamide.

The process currently used for manufacture of napropamide has been described in the prior art, U.S. Pat. No. 3,998,880, above. It starts with racemic 2-chloropropionic acid and proceeds to racemic 2-chloropropionyl diethyl amide by reacting the acid with diethylamine in the presence of phosphorus chloride. This is then followed by the reaction with α-naphthol in presence of excess of aqueous solution of alkali metal hydroxide to obtain the racemic napropamide.

The present invention, on the other hand starts from L-(−)-2-halopropionic acid to prepare D-(−)-N,N-diethyl-2-(α-naphthoxy)propionamide via L-(+)-2-halopropionyl chloride. The intermediate process steps are so selected in the process of the present invention that L-(+)-2-halo-N,N-diethyl propionamide maintains its chirality during its preparation without racemization so that the SN2 reaction at step III gives the full benefit of inversion to D-(−) chirality and optical activity.

Accordingly the present invention provides a process for the manufacture of high purity D-(−)-N,N-diethyl-2-(α-naphthoxy) propionamide including:

(i) reacting L-2-(−)halopropionic acid with a chlorinating agent, preferably thionyl chloride and dimethylformamide to form L-2-(+)-halopropionyl chloride and recovering the product using fractional distillation from the reaction mass after completion of the reaction;

(ii) reacting the L-2-(+)-halopropionyl chloride obtained at the end of step-(i), with aqueous solution of diethyl amine in presence of excess of an aqueous solution of alkali metal hydroxide in an organic solvent to form L-(+)-2-halo-N,N-diethyl propionamide and distilling out part of the solvent after completion of the reaction; and using the remaining reaction mass in situ for next step;

(iii) reacting in situ, the mass containing L-(+)-2-halo-N,N-diethyl propionamide, formed in step (ii) with α-naphthol in the presence of aqueous alkali in an organic solvent to form D-(−)-N,N-diethyl-2-(α-naphthoxy)propionamide and separating the organic phase from the aqueous phase after completion of the reaction and distilling the solvent. The product obtained was chemically and chirally more pure and was followed by recovering the product from the organic phase, by washing the said organic phase with water and removing the solvent under vacuum.

This product having chemical purity above 90% and chiral purity above 80% was further raised to higher purity product.

A process for upgrading the purity of D-(−)-N,N-diethyl-2-(α-naphthoxy)propionamide to higher purity D-(−)-N,N-diethyl-2-(α-naphthoxy)propionamide includes dissolving and crystallizing the enriched product. The D-(−)N,N-diethyl-2-(α-naphthoxy)propionamide obtained at the end of step (iii) was dissolved in a solvent, filtered and washed with chilled hexane. The solvent was removed from the crystals to obtain the crystalline D-(−)-N,N-diethyl-2-(α-naphthoxy) propionamide having chemical purity above 95%.

The process of the present invention thus provides products having high purity D-(−)-N,N-diethyl-2-(α-naphthoxy)propionamide. The process of present invention can be used to get any desired purity product but as a desirable level of purity following guidelines are useful:

(a) HIGH PURITY PRODUCT having chemical purity near about or above 90%, chiral purity near about or more than 80%; and/or (b) HIGHER PURITY PRODUCT having chemical purity near about or above 95%, chiral purity near about or more than 97%.

A process for raising high purity D-(−)-N,N-diethyl-2-(α-naphthoxy)propionamide obtained at the end of step 3 to the higher purity product having higher chemical and chiral purity.

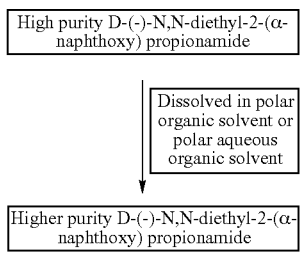

It is possible to go through the same process using different halogens like chloropropionic acid, bromopropionic acid, iodopropionic acid and the like. The use of chloro compounds is preferred for commercial scale manufacture.

The process of the present invention is useful for the large scale production of commercially feasible high purity D-(−)-N,N-diethyl-2-(α-naphthoxy)propionamide and it is neither reported nor suggested in any prior publication. The process also provides scope for further upgradation of the high purity product to higher chemical and chiral purity product.

High Purity Product

Step I: Conversion of (L)-(−)-2-halopropionic acid to (L)-(+)-2-halopropionyl chloride In this reaction, (L)-(−)-2-Halopropionic acid (L-CPA) having $[\alpha]_D^{26}$: −16.2° (neat, 1=10 cm) is reacted with excess of thionyl chloride in the presence of small amounts of dimethyl formamide to obtained a (L)-(+)-2-halopropionyl chloride.

The thionyl chloride is added at 50° C. to 60° C., preferably at 50° C. to 55° C. The reaction is carried out either with the inert organic solvents like toluene, hexane etc. or without the solvents. Preferably, reaction is carried out without the solvents. The mole ratio of the reactants—(L)-(−)-2-halopropionic acid to thionyl chloride is 1:1 to 1:1.5 moles, but the preferable ratio is 1:1.3-1:1.5 moles. The temperature of the reaction mixture is in the range of 50° C. to 60° C., preferably 58° C.-60° C. The temperatures of the reaction mixture are also very important factor for preventing the racemization.

The reaction is monitored by GC using DB-5 capillary column and goes to completion when the L-CPA content is ≦1% by area in about 5-8 hrs. After completion of the reaction, the HCl and $SO_2$ gases in the scrubber cease to evolve. The (L)-(+)-2-halopropionyl chloride is distillated from the crude mass. The liquid is distilled under atmospheric pressure using fractionating column.

The chemical purity of the distilled (L)-(+)-2-halopropionyl chloride is determined by gas chromatography and confirmed with comparison the retention time (RT) with standard sample of 2-halopropionyl chloride.

Step II: Conversion of (L)-(+)-2-halopropionyl chloride to (L)-(+)-N,N diethyl-2-halopropionamide The second step of the present invention is reaction of optically active (L)-2-(+)-halo propionyl chloride with the slight excess of diethyl amine. This reaction is carried out in by addition of (L)-(+)-2-Halopropionyl chloride into diethyl amine solution in water and an aqueous solution of an alkali metal hydroxide, preferably sodium hydroxide.

Preferably, the diethyl amine is employed 1.01-2 moles, but preferably 1.01-1.5 moles based on the one mole of (L)-(+)-2-Halopropionyl chloride. The alkali metal hydroxide is utilized in an aqueous solution of 25-50% by wt., and is present 1-3 moles per mole of (L)-(+)-2-halopropionyl chloride.

The organic solvent used for the reaction in the second step is preferably selected from non-polar solvents like benzene, toluene, xylene or mixtures thereof; more preferably toluene.

The addition of the acid chloride in to the aqueous solution of amine is done at 20 to 30° C., preferably at 25 to 27° C. The reaction mixture is generally maintained at 20 to 30° C., preferably at 25 to 27° C. The reaction is monitored by Capillary GC (DB-5) column and continued till (L)-(+)-(2)-halopropionyl chloride content is ≦0.1% by area. The reaction is generally completed within 4 to 7 hrs preferably within 4 to 5 hrs.

After completion of the reaction, the organic and aqueous layers are separated and one third to one half of the organic layer is distilled out under reduced pressure. The remaining undistilled mass containing 42 to 48% (by w/w) concentration of optically active (L)-(+)-N,N diethyl-2-halopropionamide is used as such for the next step. The chemical purity of the amide is determined using standard sample of amide and matching with retention time in gas chromatography.

Step III: Conversion of (L)-(+)-N,N diethyl-2-halo propionamide to (D)-(−)-N,N diethyl-2-(α-naphthoxy)propionamide In this step, α-naphthol is reacted with an excess of optically active (L)-(+)-N,N diethyl-2-halopropionamide obtained at the end of step II and in the presence of alkali. It is observed that the reaction of α-naphthol with (L)-(+)-N,N diethyl-2-halo propionamide is the bimolecular nucleophilic substitution ($SN_2$) type reaction accompanied by exclusive inversion of configuration. Thus, this produces N,N-diethyl-2-(α-naphthoxy)propionamide with D-configuration.

In the $SN_2$ type reaction, solvents play very vital role for preventing racemization. As reaction solvents, solvent used is selected from various non polar organic solvents like toluene, cyclohexane, and xylene or mixtures thereof. Toluene is preferred solvent.

In the preferred embodiment, the reaction of sodium salt of α-naphthol with an excess of the amide obtained at the end of step II, is carried out by addition of an aqueous solution of sodium hydroxide (25-50% by wt) into the reaction mixture.

The alkali hydroxide is present in excess. It is 1-5 moles and preferably in 2-5 moles with respect to one mole of α-naphthol. And, the amide is 1-1.5 moles per mole of α-naphthol.

The addition of the sodium hydroxide solution into the α-naphthol and the amide solution in toluene is carried out at 50° C. to 70° C., preferably at 55° C. to 57° C.

After completion of addition, reaction mass is heated to reflux at about 95° C. A temperature range from about 60° C. to 100° C. is appropriate, but considering the reaction time and other convenience, reaction mixture is generally maintained from about 90° C. to below 100° C. and preferably 95° C. to 98° C.

The reaction is monitored by gas chromatography using DB-5 capillary column. Generally the reaction is complete when the α-naphthol content is <1% (by GC area) which happens in 5 to 8 hrs, but mostly in 6 to 7 hrs. The reaction mass is then washed with water and subsequently extracted with sodium hydroxide solution and water to eliminate unreacted α-naphthol.

In order to obtain desired product in good yield and purity, the reaction between α-naphthol and amide must be carried out to completion and the excess of amide, solvents and other low boiling impurities are removed by distillation under reduced pressure.

After complete recovery of solvent, high purity D-(−)-N,N-diethyl-2-(α-naphthoxy)propionamide-is obtained as light brown solid in 84-85% yield (on mole basis of L-CPC) and has melting point of 75° C.-79° C. The chemical purity of the product is determined by gas chromatography on Packed column (10% by wt. OV-7) by using internal standard method and against pure reference standard of (D)-(−)-N,N-Diethyl-2-(α-naphthoxy)propionamide. The chiral purity is determined by normal phase HPLC using Hexane:ethanol (99:1 v/v) mobile phase and OD-H chiral column at 230 nm in UV detector.

The chemical purity of the high purity D-(−)-N,N-diethyl-2-(α-naphthoxy)propionamide solid product obtainable by this preferred embodiment of the process may be as high as of the order of 93-94%. The chiral purity as high as 81-83% of D-isomer. The Specific optical rotation (SOR) (of 1% by wt. solution in ethanol, 1=10 cm) is around $[\alpha]_D^{20}$ −86°.

The product obtained at the end of step III, is high in chemical purity and rich in chiral purity and hence can be used as napropamide concentrate in herbicidal compositions.

In order to obtain a product having higher chiral and chemical purity further upgradation of the product is carried out as described. The upgradation of the high purity material (solid, light brown color) is carried out with various organic solvents, generally aqueous polar solvent systems. Preferably, Isopropyl alcohol (IPA):water with varying ratios like 50:50 (v/v) and 70:30 (v/v) is suitable for upgradation, but other solvents can also be used.

Higher Purity Product

Upgradation of high purity D-(−)-N,N-diethyl-2-(α-naphthoxy)propionamide obtained at the end of step III to the higher purity product having higher chemical and chiral purity.

A process for upgrading high purity D-(−)-N,N-diethyl-2-(α-naphthoxy)propionamide to higher purity D-(−)-N,N-diethyl-2-(α-naphthoxy)propionamide includes dissolving and crystallizing the high purity product. The D-(−)N,N-diethyl-2-(α-naphthoxy)propionamide which is obtained at the end of step (iii) in the manufacture of high purity product is dissolved in a solvent. The crystals are filtered and washed with chilled hexane and the solvent is removed from the crystals to obtain the crystalline higher purity D-(−)N,N-diethyl-2-(α-naphthoxy)propionamide having chemical and chiral purity near about or above 95%. In this process, solvent may be selected from polar organic solvents or from polar aqueous organic solvents. The solvent is preferably isopropanol and water mixed in the ratio of 50:50 to 80:20 by volume, more preferably, in the ratio of 70:30% by volume.

The high purity product, obtained is dissolved and maintained in isopropyl alcohol:water in the vol. ratio of (65-75:35-25) preferably in the ratio of (70:30 v/v) at 60 to 65° C. with stirring for about 45 minutes. The mass is first cooled to room temperature and then to 10° C. to 12° C. and maintained at that temperature for 3 to 5 hrs for crystallization. The crystals are collected by filtration and the solid crystals are washed with chilled hexane and kept under vacuum for about 3 to 5 hrs to remove last traces of solvent moisture and the volatile impurities if any to get off-white crystalline solid with 65-66% by weight yield based on 100% by wt. of starting material L-CPC]. The melting point of the technical grade off-white solid is in the range around 94° C.-96° C. The chemical purity of the product is determined by gas chromatography on packed column (10% OV-7) by using Internal standard method and against reference standard of (D)-(−)-N,N-Diethyl-2-(α-naphthoxy)propionamide and it shows the purity to be around 96% (w/w). The chiral purity is determined by normal phase HPLC using hexane:ethanol (99:1 v/v) mobile phase and OD-H chiral column at 230 nm in UV detector and the isomer content in the solid raises to near about 98% of R-isomer and near about 2% of S-isomer. In addition to that its specific optical rotation $[\alpha]_D^{20}$ is 126° (1% by wt. solution in ethanol, 1=10 cm).

The products obtainable at the end of this step are higher purity D-(−)-N,N-diethyl-2-(α-naphthoxy)propionamide having chemical purity above 95% and chiral purity more than 97%.

The product obtained at the end of upgrading process, is higher in chemical and chiral purity and hence can be used as napropamide concentrate of higher strength, in herbicidal compositions.

EXAMPLES

The present invention will now be described with the help of following examples. Examples are for the purpose of illustration only and in no way restrict the scope of the invention.

Example 1

The process of the present invention will be illustrated in this example step by step.

STEP I: Preparation of (L)-(+)-2-chloropropionyl chloride from (L)-(−)-2-chloropropionic acid In a three-necked round bottomed kettle, (L)-(−)-2-chloropropionic acid (108.5 g, 98% chiral purity, 1.0 mole) was taken and dimethylformamide (5 ml) was added to it under continuous stirring. The temperature of the reaction mass was raised to 55° C. and thionyl chloride (178.5 g, 98% purity, 1.5 moles) was added slowly. During the addition, temperature of the reaction mass was maintained at 55° C.-57° C.

The reaction was monitored by GC using DB-5 column. The reaction got completed in 7 hrs. During the process, HCl and SO$_2$ gases evolved were absorbed in the scrubber containing dilute sodium hydroxide solution. After completion of the reaction, the evolution of the HCl and SO$_2$ gases in the scrubber had ceased. The (L)-(+)-2-chloropropionyl chloride liquid was distilled under atmospheric pressure by using a 30-cm fractionating column. The material distills at 105° C.-109° C. giving 113.0 g pure (L)-(+)-2-chloropropionyl chloride.

The chemical purity of the compound was 96% and having optical rotation: $[\alpha]_D^{26}$: +3.5° (neat, 1=10 cm.) The chemical purity of the distilled (L)-(+)-2-chloropropionyl chloride is confirmed with standard sample of 2-chloropropionyl chloride in gas chromatography.

STEP II: Preparation of (L)-(+)-N,N-diethyl-2-chloropropionamide from (L)-(+)-2-Chloropropionyl chloride A mixture of Diethyl amine (81 g, 1.1 mole, 99% pure), 48% aqueous sodium hydroxide (100 g, 1.20 mole), water (120 ml) and toluene (250 gm) were charged in to a reaction kettle. The reaction mixture was cooled up to 20° C. to 22° C. temp and L-(+)-2-chloropropionyl chloride (127 g, 1 mole) was added drop wise under continuous stirring. During the addition, temperature was not allowed to exceed beyond 30° C. and maintained until the (L)-(+)-(2)-chloropropionyl chloride was ≦0.1% by GC area. The reaction was monitored by Capillary GC (DB-5) column and completed within 5 hrs.

After completion of reaction the aqueous phase was separated and organic phase containing product in toluene was washed with water till pH of washing was neutral from the washed organic phase and the 1/3 of toluene was distilled out of the total mass. The residual organic mass was 255 g. This was found to contain 48% by weight of the (L)-(+)-2-Chloro-N,N-diethyl chloropropionamide in toluene. This corresponds to 93-94% yield of amide based on L-(+)-2-Chloropropionyl chloride. The organic mass was carried out for the next step (in situ). The chemical purity of the amide and reaction monitoring is confirmed with standard sample of (L)-(+)-N,N-diethyl chloropropionamide.

STEP III: Preparation of D-(−)-N,N-Diethyl-2-(α-naphthoxy)propionamide

Into a 3 liter round bottom kettle were placed α-Naphthol (517 g, 3.59 mole, 99% by wt. purity) and 647 g (3.95 mole) of amide obtained in step II (based on 48% purity assay w/w analysis) solution in toluene (total wt: 1345 g). The mixture was stirred and aqueous sodium hydroxide solution (642 g, 7.7 mole, 48% by wt.) was added drop wise to the reaction mass at 55-57° C. temperature.

After completion of addition, reaction mass was heated to reflux at about 95° C. When reflux began, sodium chloride began to separate out. Refluxing was continued for 6 to 7 hours till completion of the reaction <1% by GC area of α-naphthol.

The reaction mixture was cooled to 50° C. and 500 ml water and 500 ml toluene were added. The reaction mass stirred for 45 min. at this temperature. Aqueous phase, which was lighter in color than the organic phase was separated. The organic phase including the inter-phase (emulsion) was reheated to 50° C. A solution of 250 ml sodium hydroxide (5%) and 250 ml of hot water were added and the phases were separated again. The organic phase again extracted with 250 ml water. The organic layer was collected and evaporated at 80° C. under reduced pressure and then further for three hrs under high vacuum for complete removal of toluene.

After complete removal of solvent, the 850 g of high purity product was obtained which is light brown solid with 83% yield based on starting material as L-CPC and had melting point of 75° C.-79° C.

The chemical purity of the high purity product was found to be 94% by gas chromatography on packed column (10% OV-7) by using internal standard method and against reference standard of (D)-(−)-N,N-diethyl-2-(α-naphthoxy)propionamide.

When examined by normal phase HPLC using Hexane:ethanol (99:1 v/v) mobile phase and OD-H chiral column at 230 nm in UV detector, the high purity product showed 84% of D-isomer and 16% of L-isomer.

The Specific optical rotation (SOR) (of 1% solution in ethanol, 1=10 cm) is $[\alpha]_D^{20}$ −86°.

Example II

Upgradation of high purity D-(−)-N,N-diethyl-2-(α-naphthoxy)propionamide obtained at the end of step III to the higher purity product having higher chemical, and chiral purity.

This example describes upgradation of high purity product obtained in the Example I.

To the brown colour solid material obtained at the end of step III, in Example I was added 600.0 gm of isopropyl alcohol:water (70:30 v/v) mixture and it was heated at 60° C.-64° C. with constant stirring. Heating and stirring was continued till the high purity product was completely dissolved. Stirring was further continued for 45 minutes at this temperature. The mass was brought first to room temperature and then cooled to and maintained at 10° C.-12° C. for 3-4 hrs. The solid crystals were filtered and washed with chilled hexane and the solid crystals were kept under vacuum for 3 hrs. The higher purity product (690 g) was obtained at the end of step IV, as off-white crystalline solid with overall yield 66% based on starting material L-Chloropropionic acid. The melting point of the higher purity product was found to be 94.4° C.-96.1° C. The higher purity product was examined for purity by the same methods used for examining the crude product.

The chemical purity of the upgraded product was found to be 96%. The isomer ratio of the upgraded product was found to be 98% of (D-isomer) and 1.8% of (L-isomer).

The Specific Optical Rotation: $[\alpha]_D^{20}$ was found to be −126° (1% by wt. solution in ethanol, 1=10 cm).

Example III

Step I and Step II are same as in example I.

Step III: Preparation of D-(−)-N,N-Diethyl-2-(α-naphthoxy)propionamide

Into a round bottom kettle were placed α-Naphthol (1230 g, 8.45 mole, 99% purity) and 1446 g (8.37 mole) of amide obtained in step II of example I in toluene (2000 g). The mixture was stirred and aqueous sodium hydroxide solution (1534 g, 18.41 mole, 48%) was added drop wise to the reaction mass at 55° C.-57° C. temperature.

After completion of addition, reaction mass was heated to reflux at about 95° C. When reflux began, sodium chloride began to separate out. Refluxing was continued for 6 to 7 hours till completion of the reaction <1% by GC area of α-naphthol.

The reaction mixture was cooled to 50° C. and 1400 ml water was added at this temperature. The reaction mass stirred for 45 min. at this temperature and aqueous phase, which was lighter in color than the organic phase was separated. The organic phase including the inter-phase (emulsion) was reheated to 50° C. A solution of 250 ml sodium hydroxide (5%) and hot water were added and the phases were separated again. The organic phase again extracted with water. The organic layer was collected and evaporated at 80° C. under reduced pressure and then further for three hrs under high vacuum for complete removal of toluene.

After complete removal of solvent, the 2361 g of high purity product obtained which is light brown solid with 96.09% yield based on starting material as L-CPC and had melting point of 75° C.-79° C.

The chemical purity of the high purity product was found to be 86% by gas chromatography on Packed column (10% OV-7) by using internal standard method and against reference standard of (D)-(−)-N,N-diethyl-2-(α-naphthoxy)propionamide.

When examined by normal phase HPLC using Hexane:ethanol (99:1 v/v) mobile phase and OD-H chiral column at 230 nm in UV detector, the high purity product showed 84% of D-isomer and 16% of L-isomer.

The Specific optical rotation (SOR) (of 1% by wt. solution in ethanol, 1=10 cm) is $[\alpha]_D^{20}$ −78.92°

Step IV

Upgradation of high purity D-(−)-N,N-diethyl-2-(α-naphthoxy)propionamide obtained at the end of step III to the higher purity product having higher chemical and chiral purity.

This example describes upgradation of high purity product obtained in the step III of Example III.

To the brown colour solid material obtained at the end of step III, in Example III was added 5509 ml of isopropyl alcohol:water (70:30 v/v) mixture and it was heated at 60° C.-64° C. with constant stirring. Heating and stirring was continued till the high purity product was completely dissolved. Stirring was further continued for 45 minutes at this temperature. The mass was brought first to room temperature and then cooled to and maintained at 10° C.-12° C. for 3-4 hrs. The solid crystals were filtered and washed with chilled hexane and the solid crystals were kept under vacuum for 3 hrs. The higher purity product (1560 g) was obtained at the end of step II, as off-white crystalline solid with overall yield 68% based on starting material L-Chloropropionic acid. The melting point of the higher purity product was found to be 93° C.-94° C. The higher purity product was examined for purity by the same methods used for examining the crude product. The chemical purity of the upgraded product was found to be 96% (w/w). The isomer ratio of the upgraded product was found to be 98% of (D-isomer) and 1.34% of (L-isomer).

The Specific Optical Rotation: $[\alpha]_D^{20}$ was found to be −127.31° (1% by wt. solution in ethanol, l=10 cm)

Example IV

Preparation of D-(−)-N,N-diethyl-2-(α-naphthoxy)propionamide with High Purity, Higher than 99%

In 7 lit. kettle 300 g of higher pure D-(−)-N,N-diethyl-2-(α-naphthoxy)propionamide (97.5% w/w, purity) was taken and 5500 ml hexane was added to it under continuous stirring. The temperature of the reaction mass was raised to 65° C. During the addition and after the addition was over the temperature of the reaction mass was maintained at 65° C. for 2 hrs. The reaction mass was then cooled to 15° C. The solid crystals were filtered and washed with hexane. The higher purity product (237 g) was obtained. The melting point of the higher purity product was found to be 93° C.-94° C.

The chemical purity of the product was found to be 99.1%. The isomer ratio of the product was found to be 100% of D-isomer.

The Specific Optical Rotation: $[\alpha]_D^{20}$ was found to be −133.33° (1% by wt. solution in ethanol, l=10 cm)

D-(−)-N,N-diethyl-2-(α-naphthoxy)propionamide has a melting point in the range 93° C.-94° C., while racemic form of napropamide is having melting point 74.8-75.5° C. Due to the low melting point of -(−)-N,N-diethyl-2-(α-naphthoxy)propionamide, it is difficult to load high concentration of -(−)-N,N-diethyl-2-(α-naphthoxy)propionamide in the processing pan, and operate under high shear. This difficulty can be overcome by using D-(−)-N,N-diethyl-2-(α-naphthoxy)propionamide, as due to its high melting point the technical D-napropamide remains stable even after the heat generated due to shear in the manufacturing process.

Racemic form of -(−)-N,N-diethyl-2-(α-naphthoxy)propionamide is having water solubility 73 mg/litre at 20° C. while D-(−)-N,N-diethyl-2-(α-naphthoxy)propionamide is having water solubility 50 mg/1 ltr. Due to low water solubility of D-(−)-N,N-diethyl-2-(α-naphthoxy)propionamide suspension concentrate prepared using D-(−)-N,N-diethyl-2-(α-naphthoxy)propionamide is more stable. D-(−)-N,N-diethyl-2-(α-naphthoxy)propionamide suspension concentrate can be prepared as 45% SC and 50% SC. Racemic form of -(−)-N,N-diethyl-2-(α-naphthoxy)propionamide decomposes in the presence of UV radiation with colour change while D-(−)-N,N-diethyl-2-(α-naphthoxy)propionamide is stable in the presence of UV light and there is no colour change observed. Because of its UV stability the formulations prepared using D-(−)-N,N-diethyl-2-(α-naphthoxy)propionamide is physically stable and does not loose its aesthetic appeal due to color change.

Chan et al., J. Agric. Food Chem., 23(5), 1008-1010, (1975), reported that the (D)-isomer of napropamide shows 8 times more activity than the (L)-isomer and 1.7-2 times more activity than its racemic mixture, for certain weeds. Due to higher efficacy of D-(−)-N,N-diethyl-2-(α-naphthoxy)propionamide as compared to N,N-diethyl-2-(α-naphthoxy)propionamide and ease of formulating D-(−)-N,N-diethyl-2-(α-naphthoxy)propionamide even at higher concentrations e.g. 80 DF, 50 SC and so on, a highly concentrated product can be dispatched to farmers that can be diluted at the time of broadcasting as per requirement. This reduces the packaging cost and cost of transportation. This also saves the manufacturing cost as high concentrated product of D-(−)-N,N-diethyl-2-(α-naphthoxy)propionamide can be prepared using the same equipment and utilizing the same amount of energy.

Thus, a compound of this invention can be formulated as an emulsifiable concentrate, as a suspension concentrate, or as a granular formulation or formulated as any of several other known types of formulations, depending on the desired mode of application.

Emulsifiable concentrates are homogeneous liquid or paste compositions emulsifiable in water.

Granular formulations are particularly useful for aerial distribution. Useful granular formulations may be of several types. Impregnated granules are those wherein the active ingredient is applied to large particles of an absorbent carrier, such as an attapulgite or kaolin clay, corncobs, expanded mica, normally in the form of a solution in a solvent. Surface-coated granules may be produced by spraying the molten active ingredient onto the surface of a generally non-absorbent particle or by spraying on a solution of active ingredient in a solvent. The core may be water-soluble such as a prilled fertilizer, or insoluble such as sand, marble chips or coarse talc. Particularly useful is a granule wherein a wettable powder is applied as a surface coating to sand or other insoluble particles such that the wettable powder may be dispersed on contact of the granule with moisture. Granules may be produced by agglomeration of dusts or powders by compaction rollers, by extrusion through a die or by use of a granulating disc.

Granular composition of D-(−)-N,N-diethyl-2-(α-naphthoxy)propionamide can be formulated in the form of plain granules, wettable dispersible granules, wettable granules, Dispersible flowable, wettable powder and the like.

Wettable powders, dispersible and flowable formulation, are in the form of finely divided particles which disperse readily in water or other dispersants. The wettable powder is ultimately broadcasted as a finely divided dry material or as an emulsion in water or other liquid. Typical carriers for wettable powders include fuller's earth, kaolin clays, silicas and other highly absorbent, readily wet inorganic diluents. Wettable powders normally are prepared to contain about 5% to 80% of active ingredient, depending on the absorbability of the active ingredient and on the absorbency of the carrier, and usually also contain a small amount of a wetting, dispersing or emulsifying agent to facilitate dispersion.

Typical wetting, dispersing or emulsifying agents used in agricultural formulations include, for example, the alkyl and alkylaryl sulfonates and sulfates and their sodium salts; polyethylene oxides; sulfonated oils, fatty acid esters of polyhydric alcohols; and other types of surface active agents, many of which are available in commerce.

The dispersant and/or wetting agent may be chosen from any of the materials or blends of materials commonly used to disperse solid particles in water, providing that the previously mentioned compatibility requirement is satisfied. However, it has been found that consistently good results are given by taurine-type dispersion agents, for example the sodium salt of N-methyl-N-oleoyltaurate, which is available commercially under the trade name Hostapon T, (manufactured by Hoechst). In addition, the commercial wetting agent Morwet EFW, (an alkyl naphthalene sulfonate sodium salt manufactured by Witco, Morwet D809, Dallas, USA) may also be added.

D-(−)-N,N-diethyl-2-(α-naphthoxy)propionamide in the form of liquid compositions can be formulated as emulsifiable concentrate, flowable liquid, suspension concentrate and the like.

The dispersing and/or suspending agent is selected from sodium naphthalene sulphonate, alkyl naphthyl sulfonate, sodium lignosulphonate, polycarboxylates, Atlox Metasperse 550 S and other such agents known in the art.

Antifreezing agent is being used to make the formulation workable in any atmosphere. Antifreezing agents may include, but are not limited to, ethylene glycol, diethylene glycol, propylene glycol, glycerol etc.

A defoaming agent is being used to reduce the frothing. A defoaming agent may include, but is not limited to a silicon oil such as RHODASIL supplied by Rhodia Co., Precipitated Silica etc.

The inert filler may be selected from precipitated silica, kaolin, bentonite, dolomite, Attapulgite, ammonium sulphate, Attagel 50, and the like or a mixture thereof.

Viscolizing agents are selected from Xanthum Gum, celluloses, and the like or a mixture thereof.

Solvents used in the composition may be selected from cyclohexanol, pentanol, xylene, isophorone and the like or a mixture thereof.

Preservatives used in the composition may be selected from BHA, BHT, 1,2-benzisothiazolin-3-one (Proxel GXL) and the like or a mixture thereof.

These formulations may be applied without further dilution or as dilute solutions, emulsions or suspensions in water or other suitable diluent. The compositions may be applied to the area wherein control is desired by spraying in the case of liquid compositions or by distribution from mechanical equipment in the case of solids. The surface-applied material may also be blended into the upper layer of soil by cultivation, or left as applied, as is appropriate to gain the optimum results with the particular treatment.

The active herbicidal compounds of this invention may be formulated and/or applied with insecticides, fungicides, nematicides, plant growth regulators, fertilizers, and other agricultural chemicals. In applying the active compounds of this invention, whether formulated alone or with other agricultural chemicals, an effective amount and concentration of active ingredient are of course employed. The amount constituting an effective amount is variable, depending on a number of factors such as the expected pattern or rainfall or irrigation, the plant species to be controlled, and the crop, if any, to be grown. Generally, a uniform application of between 0.1 and 9 kilograms per hectare will be employed, for example, 0.25 to 4.00 kilograms per hectare.

Example IV

D-(−)-N,N-diethyl-2-(α-naphthoxy)propionamide
500 (gms/kg) DF

TABLE 1

| Sr. No. | Ingredients | % w/w |
| --- | --- | --- |
| 1. | d-(−)-N,N-diethyl-2-(α-naphthoxy)propionamide | 50 |
| 2. | Alkyl naphthalene sulfonate sodium salt | 3 |
| 3. | Styrene acrylic copolymer | 10 |
| 4. | Silicon dioxide | 3 |
| 5. | Kaolin | Q.S. |
| 6. | Total | 100 |

Process: All the ingredients given in table 1 are mixed and ground and homogenized using appropriate mill and blender to particle size d−90=10 to 15 micron.

Example V

D-(−)-N,N-diethyl-2-(α-naphthoxy)propionamide
450 SC

TABLE 2

| Sr. No. | Ingredients | % w/w |
| --- | --- | --- |
| 1 | d-(−)-N,N-diethyl-2-(α-naphthoxy)propionamide | 45 |
| 2 | alkyl naphthalene sulfonate sodium salt | 3 |
| 3 | alpha.-Hydro-.omega.-hydroxypoly(oxyethylene) poly(oxypropylene) poly (oxyethylene) block copolymer | 1 |
| 4 | Propylene Glycol | 8 |
| 5 | Silicon Emulsion | 0.2 |
| 6 | Natural clay | 0.5 |
| 7 | 1,2-Benzisothiazolin-3-one | 0.05 |
| 8 | Xanthum Gum | 1 |
| 9 | Water | q.s. |
| 10 | Total | 100 |

Process: All the ingredients of Table 2 are mixed and ground and homogenized using appropriate mill and blender to d−90=10 to 15 micron which was than agglomerated or extruded using suitable extruder to required granule size using water as binder.

The wet granules are dried and graded to required size using various sieves.

Example VI

D-(−)-N,N-diethyl-2-(α-naphthoxy)propionamide
25% (w/w) EC

TABLE 3

| Sr. No. | Ingredients | % w/w |
| --- | --- | --- |
| 1 | d-(−)-N,N-diethyl-2-(α-naphthoxy)propionamide | 26.31 |
| 2 | Calcium alkylbenzene sulphonate and Tristeryl phenol ethoxylate 16 moles | 10.00 |
| 3 | Xylene | 63.69 |
| 4 | Total | 100.0 |

Process: Required quantity of D-(−)-N,N-diethyl-2-(α-naphthoxy)propionamide is weighed and required quantity of xylene is taken in the vessel and stirred till it forms a clear solution. The required quantity of Calcium alkylbenzene sulphonate and Tristeryl phenol ethoxylate 16 moles are added and the mixture agitated for half an hour. The resulting solution is filtered and it is tested for the emulsion stability and other relevant parameters.

Example VII

D-(−)-N,N-diethyl-2-(α-naphthoxy)propionamide 15% (w/w) EW

TABLE 4

| Sr. No. | Ingredients | % w/w |
| --- | --- | --- |
| 1 | d-(−)-N,N-diethyl-2-(α-naphthoxy)propionamide | 26.31 |
| 2 | Xylene/Isophorone | 10 to 47.22 |
| 3 | Calcium alkylbenzene sulphonate and Tristeryl phenol ethoxylate 16 moles | 8 to 10.00 |
| 4 | Xanthan gum | 0.4 to 2.00 |
| 5 | 1,2-Benzisothiazolin-3-one | 0.02 to 0.5 |
| 6 | DM/Distilled Water | Q.S |
| 7 | Total | 100 gm |

Process: Required quantity of technical and solvent is weighed in the vessel and stirred till it forms a clear solution. Then required amount of Calcium alkylbenzene sulphonate and Tristeryl phenol ethoxylate 16 moles are added and agitated for half an hour. Required amount of water is added in the mixture and agitated for half an hour. 2% solution of the xanthan gum is then added in this mixture till a required viscosity is achieved. After it satisfies all requirements for an EW as per the specification, it is packed for dispatch.

It is apparent that various modifications may be made in the formulation and application of the novel compounds of this invention, without departing from the inventive concept herein, as defined in the following claims.

The invention claimed is:

1. A process for the preparation of D-(−)-N,N-diethyl-2-(α-naphthoxy) propionamide comprising in order:
    (a) reacting (L)-2-(−)halopropionic acid with a chlorinating agent and dimethylformamide to form (L)-2-(+)-halopropionyl chloride;
    (b) reacting the (L)-2-(+)-halopropionyl chloride with diethyl amine in presence of an aqueous solution of alkali metal hydroxide to form (L)-(+)-2-halo-N,N-diethyl propionamide; and
    (c) reacting the mass containing (L)-(+)-2-halo-N,N-diethyl propionamide, with α-naphthol in the presence of aqueous alkali metal hydroxide to form D-(−)-N,N-diethyl-2-α-naphthoxy)propionamide.

2. The process as claimed in claim 1, wherein said chlorinating agent is thionyl chloride.

3. The process as claimed in claim 2, wherein the mole ratio of (L)-(−)-2-halopropionic acid to thionyl chloride is from 1:1 to 1:1.5 moles.

4. The process as claimed in claim 1, wherein the temperature of the reaction mixture in step (a) is 50° C.-60° C.

5. The process as claimed in claim 1, wherein the temperature of the reaction mixture in step (a) is preferably 58° C.-60° C.

6. The process as claimed in claim 1, wherein the mole ratio of α-naphthol to (L)-(+)-2-halo-N,N-diethyl propionamide is 1:1 to 1:1.5.

7. The process as claimed in claim 1 wherein the step of reacting the mass containing (L)-(+)-2-halo-N,N-diethyl propionamide with α-naphthol is carried out in a non-polar organic solvent.

8. The process as claimed in claim 7, wherein said non-polar organic solvent is selected from a group comprising like toluene, xylene, cyclohexane and mixtures thereof.

9. The process as claimed in claim 8, wherein said non-polar organic solvent is toluene.

10. The process as claimed in claim 1, wherein said halopropionic acid used is (L)-(−)-2-chloropropionic acid.

11. A process for the preparation of high purity D-(−)-N,N-diethyl-2-α-naphthoxy)propionamide comprising: (a) reacting (L)-2-(−)halopropionic acid with a chlorinating agent and dimethylformamide to form (L)-2-(+)-halopropionyl chloride; (b) reacting the (L)-2-(+)-halopropionyl chloride with diethyl amine in presence of an aqueous solution of alkali metal hydroxide to form (L)-(+)-2-halo-N,N-diethyl propionamide; (c) reacting the mass containing (L)-(+)-2-halo-N,N-diethyl propionamide, with α-naphthol in the presence of aqueous alkali metal hydroxide to form D-(−)-N,N-diethyl-2-(α-naphthoxy)propionamide; and (d) recrystallizing the D-(−)-N,N-diethyl-2-(α-naphthoxy)propionamide in a polar organic solvent or polar aqueous organic solvent.

12. The process as claimed in claim 11, wherein said (L)-2-(+)-halopropionyl chloride obtained in step (a) is recovered by fractional distillation from the reaction mass after completion of the reaction.

13. The process as claimed in claim 11, wherein said step of recrystallizing the D-(−)-N,N-diethyl-2-(α-naphthoxy)propionamide in a polar organic solvent or polar aqueous organic solvent comprises dissolving said D-(−)-N,N-diethyl-2-(α-naphthoxy) propionamide obtained in step (c) in said polar organic solvent or polar aqueous organic solvent, filtering the resultant slurry and washing the filtered material with chilled hexane.

14. The process as claimed in claim 13, wherein the recrystallizing solvent is a mixture of isopropyl alcohol and water.

15. The process as claimed in claim 14, wherein the said isopropyl alcohol and water mixture is in the volume ratio of isopropyl alcohol:water from 50:50 to 80:20.

16. The process as claimed in claim 15, wherein said volume ratio of isopropyl alcohol:water is 70:30.

17. The process as claimed in claim 11, wherein said chlorinating agent is thionyl chloride.

18. The process as claimed in claim 11, wherein said step (c) of reacting the mass containing (L)-(+)-2-halo-N,N-diethyl propionamide with α-naphthol is carried out in a non-polar organic solvent.

19. The process as claimed in claim 18, wherein said non-polar organic solvent is selected from toluene, cyclohexane, xylene and mixtures thereof.

20. The process as claimed in claim 19, wherein said non-polar organic solvent is toluene.

21. D-(−)-N,N-diethyl-2-(α-naphthoxy)propionamide having a chiral purity of at least about 80%.

22. D-(−)-N,N-diethyl-2-(α-naphthoxy)propionamide having a chiral purity of at least about 95%.

23. D-(−)-N,N-diethyl-2-(α-naphthoxy)propionamide having a chiral purity of at least about 98%.

24. D-(−)-N,N-diethyl-2-(α-naphthoxy)propionamide having about 100% chiral purity.

25. An agrochemical composition comprising D-(−)-N,N-diethyl-2-α-naphthoxy)propionamide having a chiral purity of at least about 80% and agrochemically acceptable excipients.

26. An agrochemical composition comprising D-(−)-N,N-diethyl-2-α-naphthoxy)propionamide having a chiral purity of about 95% to about 100% and agrochemically acceptable excipients.

27. The composition as claimed in claim 25 or claim 26, wherein said composition is a granular formulation or a liquid formulation, said granular formulation being selected from impregnated granules, surface-coated granules, wettable powder, plain granules, wettable dispersible granules, wettable granules and dispersible flowable and wherein said liquid formulation is preferably selected from emulsifiable concentrate, flowable liquid, suspension concentrate and concentrated oil-in-water emulsion.

28. An agrochemical dry flowable composition comprising D-(−)-N,N-diethyl-2-(α-naphthoxy)propionamide, an alkyl naphthalene sulfonate sodium salt, a styrene acrylic copolymer, silicon dioxide and kaolin, wherein said D-(−)-N,N-diethyl-2-α-naphthoxy)propionamide has an optical purity of at least about 80% to about 100%.

29. The dry flowable composition as claimed in claim 28, wherein said D-(−)-N,N-diethyl-2-(α-naphthoxy)propionamide is present in an amount of about 50% w/w by total weight of the composition.

30. The dry flowable composition as claimed in claim 28, wherein said styrene acrylic copolymer is Atlox Metasperse 550S.

31. The dry flowable composition as claimed in claim 28, wherein said alkyl naphthalene sulfonate sodium salt is Morwet EFW.

32. An agrochemical suspension concentrate composition comprising D-(−)-N,N-diethyl-2-(α-naphthoxy)propionamide, an alkyl naphthalene sulfonate sodium salt, an α-hydro-w-hydroxypoly(oxyethylene)poly(oxypropylene)poly(oxye-thylene) block copolymer, propylene glycol, silicon emulsion, natural clay, 1,2-benzisothiazolin-3-one and xanthan gum, wherein said D-(−)-N,N-diethyl-2-(α-naphthoxy)propionamide has an optical purity of at least about 80% to about 100%.

33. The agrochemical suspension concentrate composition as claimed in claim 32, wherein said D-(−)-N,N-diethyl-2-(α-naphthoxy)propionamide is present in an amount of about 45% w/w by total weight of the composition.

34. The suspension concentrate composition as claimed in claim 32, wherein said alkyl naphthalene sulfonate sodium salt is MORWET D809.

35. The suspension concentrate composition as claimed in claim 32, wherein said natural clay is Attagel 50.

36. The suspension concentrate composition as claimed in claim 32, wherein said 1,2-benzisothiazolin-3-one is Proxel GXL.

37. An agrochemical emulsifiable concentrate composition comprising D-(−)-N,N-diethyl-2-(α-naphthoxy)propionamide, a mixture comprising calcium alkylbenzene sulfonate and tristeryl phenol ethoxylate (16 moles) and xylene, wherein said D-(−)-N,N-diethyl-2-(α-naphthoxy)propionamide has an optical purity of about 80% to about 100% and a chemical purity of about 95%.

38. The emulsifiable concentrate formulation as claimed in claim 37, wherein said D-(−)-N,N-diethyl-2-(α-naphthoxy)propionamide is present in an amount of about 25% w/w by total weight of the composition.

39. An oil-in-water concentrated emulsion composition comprising D-(−)-N,N-diethyl-2-(α-naphthoxy)propionamide, a mixture comprising calcium alkylbenzene sulfonate and tristeryl phenol ethoxylate (16 moles), a solvent selected from xylene or isophorone or combination thereof, xanthan gum and 1,2-benzisothiazolin-3-one, wherein said D-(−)-N,N-diethyl-2-(α-naphthoxy)propionamide has an optical purity of about 80% to about 100%.

40. The oil-in-water concentrated emulsion as claimed in claim 39, wherein said D-(−)-N,N-diethyl-2-(α-naphthoxy)propionamide is present in an amount of about 25% w/w by total weight of the composition.

41. An agrochemical dosage form comprising a composition as claimed in claim 25, 26, 28, 32, 37, or 39.

* * * * *